United States Patent [19]

Hörlein et al.

[11] 4,134,753
[45] Jan. 16, 1979

[54] HERBICIDAL AGENTS

[75] Inventors: Gerhard Hörlein, Frankfurt am Main; Hubert Schönowsky, Rödermark; Hermann Bieringer, Eppstein, Taunus; Peter Langelüddeke, Hofheim am Taunus, all of Fed. Rep. of Germany

[73] Assignee: Hoechst Aktiengesellschaft, Frankfurt am Main, Fed. Rep. of Germany

[21] Appl. No.: 816,700

[22] Filed: Jul. 18, 1977

[30] Foreign Application Priority Data

Jul. 20, 1976 [DE] Fed. Rep. of Germany ....... 2632581

[51] Int. Cl.² .......................... A01N 9/24; C07C 51/12
[52] U.S. Cl. .......................... 71/108; 71/100; 71/116; 71/118; 260/465 D; 260/455 R; 260/501.1; 260/501.17; 260/559 H; 260/559 T; 260/559 R; 560/9; 560/21; 562/431; 562/435; 562/471; 562/472
[58] Field of Search .............. 560/21; 260/519, 520 C; 71/108, 116

[56] References Cited

U.S. PATENT DOCUMENTS

| 3,119,682 | 1/1964 | Martin et al. ........................ 71/116 |
| 3,721,703 | 3/1973 | Nahm et al. ......................... 560/21 |
| 3,928,416 | 12/1975 | Bayer et al. ........................ 71/116 |
| 3,941,830 | 3/1976 | Theissen ............................ 560/21 |
| 4,070,177 | 1/1978 | Nishiyama et al. ................. 71/108 X |
| 4,070,178 | 1/1978 | Johnson et al. .................... 560/21 X |

FOREIGN PATENT DOCUMENTS

| 2184906 | 2/1974 | France ............................. 560/55 |
| 49-30530 | 3/1974 | Japan ............................. 560/21 |

Primary Examiner—James O. Thomas, Jr.
Assistant Examiner—G. T. Breitenstein
Attorney, Agent, or Firm—Curtis, Morris & Safford

[57] ABSTRACT

Compounds of the formula

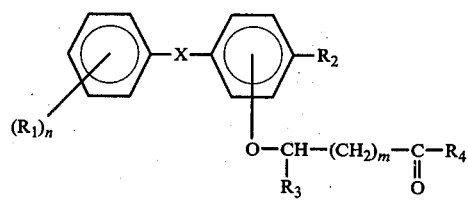

exhibit, in the pre-emergence process and in the post-emergence process, a good herbicidal action against a number of dicotyledonous weeds, they are well tolerated in monocotyledonous crops, such as wheat, barley, rice, sorghum and maize, and are also selectively active in some dicotyledonous crops such as soy beans, groundnuts and the like.

14 Claims, No Drawings

HERBICIDAL AGENTS

The present invention relates to compounds of the general formula

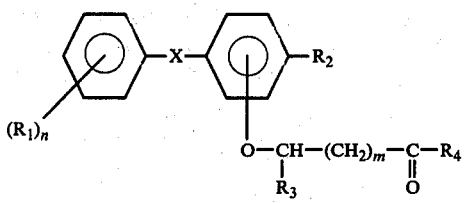

in which $R_1$ is halogen, $(C_1-C_4)$-alkyl, $NO_2$ or CN, $R_2$ is $NO_2$, CN or $CF_3$, n is 1 to 3, m is 0 to 2, X is O or S, $R_3$ is $(C_1-C_4)$-alkyl, $R_4$ is OH, $(C_1-C_8)$-alkoxy which may be substituted by halogen, $(C_1-C_2)$-alkoxy and/or hydroxyl, or is $(C_1-C_6)$-alkylthio, $(C_3-C_6)$-alkenyloxy, $(C_3-C_6)$-alkinyloxy, $(C_5-C_8)$-cycloalkyloxy, $(C_5-C_8)$-cycloalkenyloxy, amino, hydrazino, $(C_1-C_4)$-alkylamino, di-$(C_1-C_4)$-alkylamino, phenylamino, phenoxy or phenylthio (in which the phenyl radical may also be substituted by halogen, $CF_3$, $CH_3$, OH and/or $(C_1-C_2)$-alkoxycarbonyl), or denotes the —OCat. group, where Cat. is the cation of an inorganic or organic base.

Preferred meanings of the radicals are: $R_1$ = halogen, especially Cl or Br; $R_2$ = $NO_2$; $R_3$ = $CH_3$; $R_4$ = $(C_3-C_8)$-alkoxy, which may be substituted, especially monosubstituted or disubstituted, by halogen and/or $(C_1-C_2)$-alkoxy, or $R_4$ = $NH_2$, OH or OCat., with Cat preferably denoting an alkali metal cation, for example $Na^+$ or $K^+$, ammonium or the cation of an organic base, such as, for example, dimethylamine or ethanolamine. n is preferably 1 or 2 and m is preferably 0 or 1.

The compounds according to the invention can be manufactured by reacting phenoxyphenols of the formula

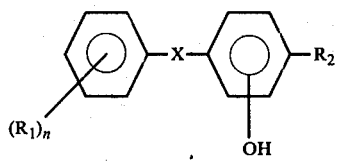

if appropriate in the presence of an acid-binding agent, or reacting corresponding phenolates, with carboxylic acid derivatives of the formula

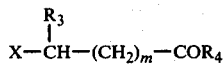

wherein X represents halogen, and converting the compounds of the forumla (I) thus obtained, if desired, into other functional derivatives of the formula (I) by esterification, saponification, salt formation, trans-esterification or amidation.

In the formula (III), X preferably denotes chlorine or bromine. Accordingly, the starting materials used are above all 2-bromopropionic acid, 2-chloropropionic acid and their derivatives.

The reaction is advantageously carried out in an organic solvent. The solvents used are advantageously ketones, such as acetone or diethyl ketone, carboxylic acid amides, such as dimethylformamide, sulfoxides, such as dimethylsulfoxide, or aromatic hydrocarbons, such as benzene or toluene. If free phenols of the formula (II) are used as starting materials, the reaction is carried out in the presence of an alkaline compound in order to bind the hydrogen halide liberated, such as, for example, potassium carbonate or a tertiary organic base, for example triethylamine.

After completion of the reaction, the hydrogen halide salt formed is removed by filtration or treatment with water and, after subsequently removing the organic solvent, if appropriate, the ester formed, or other derivatives of the carboxylic acid obtained, are isolated.

The derivatives thus obtained can be purified in accordance with customary processes, for example by distillation or by recrystallisation from organic solvents, which solvents may be mixed with water.

The various functional derivatives of the formula (I) can be converted into one another in a manner which is in itself known. For example, carboxylic acid esters obtained can be saponified with alkali, in which case it is advantageous to use aqueous alkali metal hydroxide solutions in the presence of lower alcohols, and to warm the mixture. The alkaline solution is finally acidified, whereupon the free acids separate out in a crystalline or oily form.

The free acids of the formula (I) obtained by saponification or by preparation from free halogenopropionic acids ($R_4$ = OH) can subsequently be converted into other esters in the usual manner. This is best done in the presence of catalytic amounts of an acid, such as sulfuric acid, toluenesulfonic acid or hydrochloric acid, or in the presence of other acid catalysts. Amongst the latter, Lewis acids, such as boron trifluoride, or acid ion exchangers, should be mentioned.

It is also possible to use, for the esterification, the acid chlorides which are easily accessible, for example by reacting the carboxylic acids of the formula (I) with inorganic acid chlorides, for example thionyl chloride, and which, with the said alcohols, give the corresponding esters.

Further derivatives of the formula (I) are obtained by reacting the acid chlorides or esters with amines or anilines.

The starting materials of the formula (II) are obtained, for example, by first preparing the corresponding diphenyl ethers from substituted phenols and chloroanisoles and then converting these by an ether scission, in a manner which is in itself known, into the desired phenoxyphenols.

The substances according to the invention exhibit, in the pre-emergence process and in the post-emergence process, a good herbicidal action against a number of dicotyledonous weeds which represent economically important problems in a great diversity of agricultural regions of the earth. In particular, they successfully combat species which are difficult to combat, such as cleavers (Galium) and Ipomoea, which are important harmful plants in the European climatic zone, on the one hand, and the sub-tropical/tropical culture regions, on the other hand, in addition to combating numerous other species of weeds. The compounds according to the invention are distinguished by being particularly well tolerated in monocotyledonous crops, such as wheat, barley, rice, sorghum and maize, but are also selectively active in some dicotyledonous crops such as soy beans, groundnuts and the like. In the said cultures, no damage whatsoever is observed even at concentrations of 2.5 kg/ha. Under advantageous conditions such as, for example, in water rice cultures, monocotyledonous weeds are also combated successfully in monocotyledonous crop plants, examples of such weeds being perennial sedges (Eleocharis) or annual plants such as Echinochloa and annual species of sedge.

The compounds can therefore be used for the manufacture of herbicidal agents, which contain 2 – 95% of the active compounds of the formula (I). These agents can be employed as emulsifiable concentrates, wettable powders, sprayable solutions, dusting agents and granules, in the form of the customary preparations.

Wettable powders are formulations which are uniformly dispersible in water and which, in addition to the active compound, also contain diluents or inert materials, wetting agents, for example, polyoxyethylated alkylphenols, polyoxyethylated oleylamines or stearylamines, alkylsulfonates or alkylphenylsulfonates and dispersing agents, for example sodium ligninsulfonates, sodium 2,2'-dinaphthylmethane-6,6'-disulfonate or the sodium salt of oleyl-methyl-taurine.

Emulsifiable concentrates are obtained by dissolving the active compound in an organic solvent, for example butanol, cyclohexanone, dimethylformamide, xylene or even higher-boiling aromatics, and adding a non-ionic wetting agent (emulsifier), for example a polyoxyethylated alkylphenol or a polyoxyethylated oleylamine or stearylamine.

Dusting agents are obtained by grinding the active compound with finely divided solids, for example talc, natural clays, such as kaolin, bentonite, pyrophillite or diatomaceous earth.

Sprayable solutions, such as are extensively marketed in aerosol cans, contain the active compound dissolved in an organic solvent, in addition to, for example, a mixture of fluorochlorohydrocarbons as the propellant.

Granules can be manufactured either by spraying the active compound onto adsorbent, granular inert material or by applying active compound concentrates by means of adhesives, for example polyvinyl alcohol, sodium polyacrylate or even mineral oils, onto the surfaces of carriers, such as sand, kaolinites or granular inert material. Suitable active compounds can also be manufactured by the customary methods of manufacture of fertilizer granules, if desired using a mixture with fertilizers.

In the case of herbicidal agents, the concentrations of the active compounds in the commercial formulations can vary. In wettable powders, the active compound concentration varies, for example, between about 10% and 95%, and the remainder consists of the abovementioned formulation additives. In the case of emulsifiable concentrates, the active compound concentration is about 10% to 80%. Dust formulations contain in most cases 5 – 20% of active compound, and sprayable solutions about 2 – 20%. In the case of granules, the active compound content in part depends on whether the active compound is in a liquid or solid form and what granulating auxiliaries, fillers and the like are used.

For use, the commercial concentrates are, if appropriate, diluted in the usual manner, for example by means of water in the case of wettable powders and emulsifiable concentrates. Formulations in the form of dusts and granules, and sprayable solutions are not diluted further, with additional inert materials, before use. The amount required to be used varies with the external conditions such as temperature, humidity and the like.

The amount can vary within wide limits, for example between 0.1 and 10.0 kg/ha of active substance but is preferably between 0.3 and 5 kg/ha.

The active compounds according to the invention can be combined with other herbicides and soil insecticides.

Another form of using the active compounds in question is to mix it with fertilizers, whereby combined fertilizing and herbicidal agents are obtained.

FORMULATION EXAMPLES

Example A

A wettable powder which is easily dispersible in water is obtainable by mixing 25 parts by weight of isobutyl 2-[3-(2',4'-dichlorophenoxy)-6-nitrophenoxy]-propionate as the active compound, 64 parts by weight of quartz, containing kaolin, as an inert material, 10 parts by weight of potassium ligninsulfonate and 1 part by weight of the sodium salt of oleyl-methyl-taurine as wetting agent and dispersing agent, and grinding the mixture in a pin mill.

Example B

A dusting agent which is very suitable for use as a weed-killer is obtained by mixing 10 parts by weight of isobutyl 2-[3-(2',4'-dichlorophenoxy)-6-nitrophenoxy]-propionate as the active compound and 90 parts by weight of talc as the inert material, and comminuting the mixture in a hammer mill.

Example C

An emulsifiable concentrate consists of 15 parts by weight of isobutyl 2-[3-(2',4'-dichlorophenoxy)-6-nitrophenoxy]-propionate, 75 parts by weight of cyclohexanone as the solvent and 10 parts by weight of oxyethylated nonylphenol (10 molecules of ethylene oxide) as the emulsifier.

Example D

Granules consist, for example, of about 2 – 15 parts by weight of isobutyl 2-[3-(2',4'-dichlorophenoxy)-6-nitrophenoxy]-propionate and inert granule carriers, such as, for example, attapulgite, pumice granules and quartz sand.

PREPARATION EXAMPLES

General instruction for phenoxyphenoxycarboxylic acid esters of the general formula I Example A 0.1 mole of phenol (II) is dissolved in 50 ml of methyl ethyl ketone, 0.11 mole of (anhydrous) potassium carbonate is added and 0.11 mole of halogenocarboxylic acid ester (III) is added dropwise. The mixture is then heated under reflux for about 16 hours. Thereafter ice water is added, the product is taken up in methylene chloride, the organic phase is dried over $Na_2SO_4$, the solvent is distilled off and the crude product of the general formula (I) is either caused to crystallize or distilled in vacuo.

Example B 0.1 mole of the ester from Example A is dissolved in 270 ml of methanol, 24 ml of 45% strength sodium hydroxide solution are added dropwise and the mixture is heated for 2 hours under reflux. The solvent is then distilled off and the corresponding acid is isolated as the sodium salt. The free acid is liberated by means of dilute hydrochloric acid.

Example C (a) 0.1 mole of the acid from Example B and 80 ml of thionyl chloride are mixed and heated for 6 hours under reflux. The excess thionyl chloride is then distilled off and the acid chloride is taken up in toluene.

(b) 0.1 mole of sodium hydroxide, dissolved in 50 ml of water, is added to 0.1 mole of an alcohol ($HOR_4$) dissolved in 50 ml of toluene. 0.1 mole of acid chloride from Example C, dissolved in toluene, are added dropwise at about 25° – 40° C. After about 1 hour, the toluene solution is separated off, washed with water and dried over potassium carbonate. After distilling off the solvent, the crude product thus obtained, which corresponds to the general formula (I), is caused to crystallize or is purified by distillation.

Example D 0.2 mole of hydrazine solution (80% strength) is taken and 50 ml of toluene are added. 0.1 mole of acid chloride according to Example C, in 50 ml of toluene, is then added dropwise at about 30° C. After completion of the reaction, the toluene phase is separated off, washed with water and dried over sodium sulfate. After distilling off the toluene, the hydrazide is isolated.

Example E 0.1 mole of triethylamine is added to 0.1 mole of acid chloride (prepared according to Example C), dissolved in 50 ml of toluene. 0.1 mole of an aliphatic amine or of an aniline is then added dropwise at 25°-40° C. The mixture is allowed to react for a further hour and water is then added. The toluene phase is separated off and washed with water and dried over sodium sulfate. After distilling off the toluene, the amide or anilide is isolated.

The compounds thus obtained, of the formula

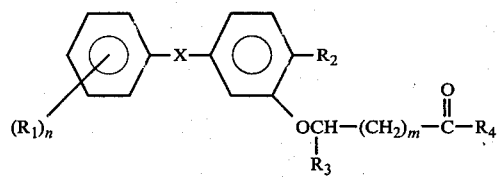

are listed in the table which follows.

TABLE 1

| Example No. | $(R_1)_n$ | X | $R_2$ | $R_3$ | m | $R_4$ | m.p./b.p./$n_D$ analysis | Instruction |
|---|---|---|---|---|---|---|---|---|
| 1 | 4-Cl | O | $NO_2$ | $-CH_3$ | 0 | $-OCH_3$ | m.p. 77–78° C | A |
| 2 | 4-Cl | O | $NO_2$ | $-CH_3$ | 0 | $-OC_2H_5$ | m.p. 70–71° C | A |
| 3 | 4-Cl | O | $NO_2$ | $-CH_3$ | 0 | $-OCH(CH_3)_2$ | m.p. 82–84° C | A |
| 4 | 2,4-Cl | O | $NO_2$ | $-CH_3$ | 0 | $-OCH_2-CH(CH_3)_2$ | b.p.$_{0.2}$: 203–204° C | A |
| 5 | 2,4-Cl | O | $NO_2$ | $-CH_3$ | 0 | $-OCH_3$ | m.p. 76–79° C | A |
| 6 | 2,4-Cl | O | $NO_2$ | $-CH_3$ | 0 | $-OC_2H_5$ | m.p. 88–89° C | A |
| 7 | 2,4-Cl | O | $NO_2$ | $-CH_3$ | 0 | $-OCH(CH_3)_2$ | m.p. 66–67° C | A |
| 8 | 2,4-Cl | O | $NO_2$ | $-CH_3$ | 0 | $-OCH_2-CH(CH_3)_2$ | b.p.$_{0.2}$: 211–213° C | A |
| 9 | 2,4-Cl | O | $NO_2$ | $-CH_3$ | 0 | $-O-CH(CH_3)-C_2H_5$ | — | A |
| 10 | 2,4-Cl | O | $NO_2$ | $-CH_3$ | 0 | $-O-CH_2-CH(C_2H_5)-C_4H_9$ | $n_D^{24}$: 1.5391 | A |
| 11 | 2,4-Cl | O | $NO_2$ | $-CH_3$ | 0 | $-O-CH_2-CH_2-Cl$ | — | C |
| 12 | 2,4-Cl | O | $NO_2$ | $-CH_3$ | 0 | $-O(CH_2)_2-OCH_3$ | calc. C:50.2% H:4.0% found C:49.9% H:4.2% | A |
| 13 | 2,4-Cl | O | $NO_2$ | $-CH_3$ | 0 | $-OCH_2-CH=CH_2$ | m.p. 84–87° C | A |
| 14 | 2,4-Cl | O | $NO_2$ | $-CH_3$ | 0 | $-O-CH_2-C\equiv CH$ | $n_D^{22}$: 1.5759 | C |
| 15 | 2,4-Cl | O | $NO_2$ | $-CH_3$ | 0 | $-O-C_6H_{11}$ | m.p. 56–59° C | A |
| 16 | 2,4-Cl | O | $NO_2$ | $-CH_3$ | 0 | $-OH$ | m.p. 109–110° C | B |
| 17 | 2,4-Cl | O | $NO_2$ | $-CH_3$ | 0 | $-O^\ominus Na^\oplus$ | m.p. 100–115° C | B |
| 18 | 2,4-Cl | O | $NO_2$ | $-CH_3$ | 0 | $-O^\ominus H\overset{\oplus}{N}(CH_3)_2$ | m.p. 118–121° C | B |
| 19 | 2,4-Cl | O | $NO_2$ | $-CH_3$ | 0 | $-NH_2$ | m.p. 155–157° C | E |
| 20 | 2,4-Cl | O | $NO_2$ | $-CH_3$ | 0 | $-NH-NH_2$ | m.p. 116–120° C | D |
| 21 | 2,4-Cl | O | $NO_2$ | $-CH_3$ | 0 | $-N(CH_3)(C_4H_9(n))$ | $n_D^{24}$: 1.5745 | E |
| 22 | 2,4-Cl | O | $NO_2$ | $-CH_3$ | 0 | $-NH-C_2H_5$ | m.p. 113–116° C | E |
| 23 | 2,4-Cl | O | $NO_2$ | $-CH_3$ | 0 | $-S-C_6H_4-Cl$ | $n_D^{24}$: 1.6335 | C |
| 24 | 2,4-Cl | O | $NO_2$ | $-CH_3$ | 0 | $-O-C_6H_4-CH_3$ | m.p. 98–99° C | C |
| 25 | 2,4-Cl | O | $NO_2$ | $-CH_3$ | 0 | $-NH-C_6H_4-CF_3$ | m.p. 159–160° C | D |
| 26 | 2,4-Cl | O | $NO_2$ | $-CH_3$ | 0 | $-NH-C_6H_4-OH$ | m.p. 196–199° C | D |
| 27 | 2,4,6-Cl | O | $NO_2$ | $-CH_3$ | 0 | $-OCH_2-CH(CH_3)_2$ | — | A |
| 28 | 2,4,6-Cl | O | $NO_2$ | $-C_2H_5$ | 0 | $-OCH(CH_3)_2$ | — | A |
| 29 | 2,4,6-Cl | O | $NO_2$ | $-CH_3$ | 0 | $-OH$ | — | B |
| 30 | 2,4,6-Cl | O | $NO_2$ | $-CH_3$ | 0 | $-NH_2$ | — | E |
| 31 | 2,4-Cl | O | CN | $-C_2H_5$ | 0 | $-OC_2H_5$ | — | A |

TABLE 1-continued

| Example No. | (R₁)ₙ | X | R₂ | R₃ | m | R₄ | m.p./b.p./n_D analysis | Instruction |
|---|---|---|---|---|---|---|---|---|
| 32 | 2,4-Cl | O | CN | —CH₃ | 0 | —OCH₂CH(CH₃)₂ | — | A |
| 33 | 2,4-Cl | O | CN | —CH₃ | 0 | —OH | — | B |
| 34 | 2,4-Cl | O | NO₂ | —CH₃ | 1 | —OCH₃ | — | C |
| 35 | 2,4-Cl | O | NO₂ | —CH₃ | 1 | —OCH₂—CH(CH₃)₂ | — | C |
| 36 | 2,4-Cl | O | NO₂ | —CH₃ | 1 | —O(CH₂)₂—OCH₃ | — | C |
| 37 | 2,4-Cl | O | NO₂ | —CH₃ | 0 | —O—C₂H₅ | — | A |
| 38 | 2,4,-Cl | S | NO₂ | —CH₃ | 0 | —O—CH₂CH(CH₃)₂ | calc. N: 2.8% Hal: 14.2% found N: 2.0 Hal: 14.5% | A |
| 39 | 2-Cl, 4-Br | O | NO₂ | —CH₃ | 0 | —O—C₆H₁₃(n) | — | A |
| 40 | 2-Cl, 4-Br | O | NO₂ | —C₂H₅ | 0 | —O—C₄H₉(n) | — | A |
| 41 | 2-Cl, 4-Br | O | NO₂ | —CH₃ | 1 | —OC₂H₅ | — | C |
| 42 | 2-Cl, 4-Br | O | NO₂ | —CH₃ | 1 | —OH | — | B |
| 43 | 2-Cl, 4-Br | O | CN | —CH₃ | 0 | —O—CH₂—CH(CH₃)₂ | — | A |
| 44 | 2-Cl, 4-Br | O | CN | —CH₃ | 0 | —OCH(CH₃)₂ | — | A |
| 45 | 2-Cl, 4-Br | S | NO₂ | —CH₃ | 0 | —OC₄H₉(n) | — | A |
| 46 | 2-Cl, 4-Br | S | NO₂ | —CH₃ | 0 | —O—C₆H₁₃(n) | — | A |
| 47 | 2,4,6-Cl | O | CN | —C₂H₅ | 0 | —OH | — | B |
| 48 | 2,4,6-Cl | O | CN | —CH₃ | 0 | —OC₂H₅ | — | A |
| 49 | 2,4,6-Cl | S | CN | —CH₃ | 0 | —OCH(CH₃)₂ | — | A |
| 50 | 2-Cl, 4-Br | O | NO₂ | —CH₃ | 0 | —OCH₃ | m.p. 84–86° C | A |
| 51 | 2-Cl, 4-Br | O | NO₂ | —CH₃ | 0 | —OCH(CH₃)₂ | m.p. 65–66° C | A |
| 52 | 2-Cl, 4-Br | O | NO₂ | —CH₃ | 0 | —OCH₂—CH=CH₂ | m.p. 68° C | A |
| 53 | 2-Cl, 4-Br | O | NO₂ | —CH₃ | 0 | —O—CH₂—CH(CH₃)₂ | m.p. 53–54° C | A |
| 54 | 2-Cl, 4-Br | O | NO₂ | —CH₃ | 0 | —O—CH(CH₃)—C₂H₅ | m.p. 59–61° C | A |
| 55 | 2-Cl, 4-Br | O | NO₂ | —CH₃ | 0 | —O—C₆H₁₁ (cyclohexyl) | m.p. 51–52° C | A |
| 56 | 4-Br | O | NO₂ | —CH₃ | 0 | —OCH₃ | m.p. 77–80° C | A |
| 57 | 4-Br | O | NO₂ | —CH₃ | 0 | —OC₂H₅ | m.p. 53–56° C | A |
| 58 | 4-Br | O | NO₂ | —CH₃ | 0 | —OC₃H₇(n) | m.p. 50–51° C | A |
| 59 | 4-Br | O | NO₂ | —CH₃ | 0 | —O—CH₂—CH=CH₂ | n_D²²: 1.5965 | A |
| 60 | 4-Br | O | NO₂ | —CH₃ | 0 | —O—CH₂—CH(CH₃)₂ | n_D²⁴: 1.5672 | A |
| 61 | 4-Br | O | NO₂ | —CH₃ | 0 | —O—CH(CH₃)—C₂H₅ | m.p. 58–60° C | A |
| 62 | 4-Br | O | NO₂ | —CH₃ | 0 | —O—C₆H₁₃(n) | N_D²³: 1.5671 | A |
| 63 | 4-Br | O | NO₂ | —CH₃ | 0 | —O—C₆H₁₁ (cyclohexyl) | m.p. 63–64° C | A |
| 64 | 2,4-Br | O | NO₂ | —CH₃ | 0 | —O—(CH₂)₂—OCH₃ | n_D²⁴: 1.5961 | A |
| 65 | 2,4-Br | O | NO₂ | —CH₃ | 0 | —O—CH₂—CH(CH₃)₂ | calc. N:2.7%, Br:31.0% found N:2.6%, Br:31.3% | A |
| 66 | 2,4 BR | O | NO₂ | —CH₃ | 0 | —O—CH₂—CH(C₂H₅)—C₄H₉(n) | n_D²⁵: 1.5632 | A |

TABLE 2

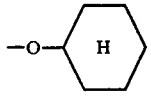

B:

| Example No. | (R₁)ₙ | X | R₂ | R₃ | m | R₄ | m.p./b.p./n_D | Instruction |
|---|---|---|---|---|---|---|---|---|
| 67 | 2,4-Cl | O | NO₂ | —CH₃ | 0 | —O—CH₂—CH(CH₃)₂ | b.p.₀.₃: 212–218° C | A |
| 68 | 2,4-Cl | O | NO₂ | —CH₃ | 1 | —O—C₃H₇(m) | — | A |
| 69 | 2,4-Cl | O | CN | —CH₃ | 0 | —O—CH₂—CH₂—Cl | — | C |
| 70 | 2,4-Cl | S | NO₂ | —CH₃ | 0 | —O—C₄H₉(n) | — | A |
| 71 | 2-Cl, 4-Br | O | NO₂ | —CH₃ | 0 | —OH | — | B |
| 72 | 2-Cl, 4-Br | O | NO₂ | —CH₃ | 1 | —O—CH₂CH(CH₃)₂ | — | C |
| 73 | 2-Cl, 4-Br | O | CN | —CH₃ | 0 | —OC₄H₉(n) | — | A |
| 74 | 2-Cl, 4-Br | S | NO₂ | —CH₃ | 0 | —O(CH₂)₂—OCH₃ | — | A |
| 75 | 2,4,6-Cl | O | NO₂ | —C₂H₅ | 0 | —OCH₃ | — | A |
| 76 | 2,4,6-Cl | O | NO₂ | —CH₃ | 1 | —O—C₆H₁₁ (cyclohexyl) | — | A |
| 77 | 2,4,6-Cl | O | CN | —CH₃ | 0 | —OC₂H₅ | — | A |
| 78 | 2,4,6-Cl | S | NO₂ | —CH₃ | 0 | —OH | — | B |
| 79 | 2,4-Cl | O | NO₂ | —CH₃ | 0 | —O—CH(CH₃)—C₂H₅ | b.p.₀.₃: 207–210° C | A |
| 80 | 2-Cl, 4-Br | O | NO₂ | —CH₃ | 0 | —OC₂H₅ | — | A |
| 81 | 2,4,6-Cl | O | NO₂ | —CH₃ | 0 | —O—CH(CH₃)₂ | — | A |
| 82 | 4-F | O | NO₂ | —CH₃ | 0 | —O—C₄H₉(n) | — | A |

TABLE 2-continued

B: structure with (R₁)ₙ-phenyl-X-phenyl(R₂)(O-CH(CH₃)-(CH₂)ₘ-C(=O)-R₄)

| Example No. | (R₁)ₙ | X | R₂ | R₃ | m | R₄ | m.p./b.p./$n_D$ | Instruction |
|---|---|---|---|---|---|---|---|---|
| 83 | 4-Br | O | NO₂ | —CH₃ | 0 | —O—CH(CH₃)—C₂H₅ | $n_D^{22}$: 1.5813 | A |
| 84 | 2-CH₃, 4-Cl | O | NO₂ | —CH₃ | 0 | —O—CH₂—CH(CH₃)₂ | — | A |
| 85 | 4-CN | O | NO₂ | —CH₃ | 0 | —OCH₃ | — | A |
| 86 | 4-CH(CH₃)₂ | O | NO₂ | —CH₃ | 0 | —OH | — | B |
| 87 | 2,4-Cl | O | NO₂ | —CH₃ | 0 | —OCH₃ | b.p.$_{0.23}$: 195–197° C | A |
| 88 | 2,4-Cl | O | NO₂ | —CH₃ | 0 | —O—CH₂—CH=CH₂ | b.p.$_{0.7}$: 230–231° C | A |
| 89 | 2,4-Cl | O | NO₂ | —CH₃ | 0 | —O—CH₂—CH(C₂H₅)—C₄H₉(n) | $n_D^{24}$: 1.5502 | A |
| 90 | 2,4-Cl | O | NO₂ | —CH₃ | 0 | —O—C₆H₁₁(H) (cyclohexyl) | $n_D^{28}$: 1.5728 | A |
| 91 | 2-Cl, 4-Br | O | NO₂ | —CH₃ | 0 | —OCH₃ | $n_D^{23}$: 1.5815 | A |
| 92 | 2-Cl, 4-Br | O | NO₂ | —CH₃ | 0 | —O—CH₂—CH=CH₂ | $n_D^{23}$: 1.5775 | A |
| 93 | 2-Cl, 4-Br | O | NO₂ | —CH₃ | 0 | —O—CH₂—CH(CH₃)₂ | $n_D^{23}$: 1.5732 | A |
| 94 | 2-Cl, 4-Br | O | NO₂ | —CH₃ | 0 | —O—C₆H₁₁(H) (cyclohexyl) | $n_D^{23}$: 1.5615 | A |
| 95 | 2-Cl, 4-Br | O | NO₂ | —CH₃ | 0 | —O—C₆H₁₃(n) | $n_D^{23}$: 1.5625 | A |
| 96 | 4-Br | O | NO₂ | —CH₃ | 0 | —OCH₃ | $n_D^{22}$: 1.6032 | A |
| 97 | 4-Br | O | NO₂ | —CH₃ | 0 | —OC₂H₅ | $n_D^{22}$: 1.5911 | A |
| 98 | 4-Br | O | NO₂ | —CH₃ | 0 | —OC₃H₇(n) | $n_D^{22}$: 1.5838 | A |
| 99 | 4-Br | O | NO₂ | —CH₃ | 0 | —O(CH₂)₂—OCH₃ | $n_D^{22}$: 1.5912 | A |
| 100 | 4-Br | O | NO₂ | —CH₃ | 0 | —O—CH₂—CH(CH₃)₂ | $n_D^{22}$: 1.5795 | A |
| 101 | 4-Br | O | NO₂ | —CH₃ | 0 | —O—C₆H₁₁(H) (cyclohexyl) | calc. N:2.9%, Br:16.8% found N:3.0%, Br:17.1% | A |
| 102 | 2,4-Br | O | NO₂ | —CH₃ | 0 | —O—CH₂—CH(CH₃)₂ | $n_D^{24}$: 1.5871 | A |
| 103 | 2,4-Br | O | NO₂ | —CH₃ | 0 | —O—CH₂—CH(C₂H₅)—C₄H₉(n) | $n_D^{25}$: 1.5670 | A |
| 104 | 2,4-Br | O | NO₂ | —CH₃ | 0 | —O—C₆H₁₁(H) (cyclohexyl) | $n_D^{24}$: 1.5903 | A |

USE EXAMPLES

EXAMPLE I: (Pre-emergence)

To test the soil action, the compounds claimed were sprayed, in the pre-emergence method, onto pots in which various species of weeds had been sown beforehand. After application of the substances, the pots were set up in a greenhouse and the herbicidal action on the test plants was rated repeatedly. The final evaluation was made 4 weeks after treatment and gave the results shown in Table I.

The following were used as comparative agents
A Bifenox (Modown)

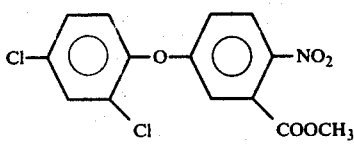

B 2,4-Dichlorophenyl 3-methoxy-4-nitrophenyl ether

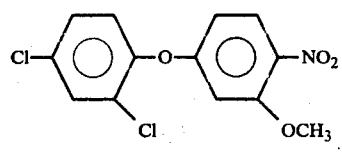

The result of the treatment was determined, as also in the subsequent examples, by rating in accordance with the BOLLE scheme (Nachr.blatt des Dt. Pflanzenschutzdienstes 16, 1964, 92–94).

It was found that the compounds claimed have a good herbicidal activity against harmful weeds even in low doses. Above all, they prove very superior in combating Chrysanthemum.

| Figure of merit | Bolle rating scheme Damage in % to | | | | |
|---|---|---|---|---|---|
| | weeds | | | crop plants | |
| 1 | | 100 | | 0 | |
| 2 | 97.5 | to | <100 | >0 | to 2.5 |
| 3 | 95 | " | <97.5 | >2,5 | " 5 |
| 4 | 90 | " | <95 | >5 | " 10 |
| 5 | 85 | " | 90 | >10 | " 15 |
| 6 | 75 | " | <85 | >15 | " 25 |
| 7 | 65 | " | <75 | >25 | " 35 |
| 8 | 32.5 | " | 65 | >35 | " 67.5 |
| 9 | 0 | " | <32.5 | >67.5 | " 100 |

EXAMPLE II (Post-emergence)

To test the leaf action, the compounds were sprayed onto already emerged weeds, about 8–15 cm in height, which had been grown in pots. Thereafter, the herbicidal action in a greenhouse was rated, again at intervals of 3 weeks. This showed, as presented in Table II, that the activity against virtually all the harmful weeds tested was superior to that of the comparative substances. Species of weeds which are particularly difficult to combat, such as chrysanthemum, Ipomoea and others, were dealt with substantially more effectively.

TABLE I:

Comparison of the action against broad-leaved weeds, in the pre-emergence method

| Product | kg of active substance/ha | Sinapis | Galium | Chenopodium | Matricaria | Stellaria | Amaranthus | Ipomoea | Chrysanthemum |
|---|---|---|---|---|---|---|---|---|---|
| | 2.5 | 1 | 2 | 1 | 1 | 3 | 1 | 2 | 1 |
| 5 | 0.6 | 6 | 3 | 1 | 1 | 8 | 1 | 5 | 1 |
| | 2.5 | 7 | 1 | — | — | 8 | 1 | 8 | 1 |
| 6 | 0.6 | 8 | 7 | — | — | 9 | 1 | 9 | 1 |
| | 2.5 | 8 | 3 | — | — | 7 | 1 | 7 | 1 |
| 7 | 0.6 | 9 | 8 | — | — | 9 | 1 | 9 | 2 |
| | 2.5 | 2 | 1 | 1 | 1 | 3 | 1 | 5 | 1 |
| 8 | 0.6 | 7 | 2 | 1 | 1 | 7 | 1 | 6 | 1 |
| | 2.5 | 8 | 1 | 1 | 1 | 8 | 1 | 8 | 3 |
| A | 0.6 | 9 | 5 | 1 | 1 | 9 | 1 | 9 | 6 |
| | 2.5 | 1 | — | — | 4 | 8 | 1 | 9 | 6 |
| B | 0.6 | 9 | — | — | 7 | 8 | 2 | 9 | 8 |

TABLE II:

Comparison of action in the post-emergence method (Rating 3 weeks after application)

| Product | kg of active substance/ha | Sinapis | Galium | Chenopodium | Matricaria | Chrysanthemum | Stellaria | Amaranthus | Ipomoea |
|---|---|---|---|---|---|---|---|---|---|
| | 2.5 | 6 | 4 | 1 | 1 | 1 | 8 | 1 | 5 |
| 5 | 0.6 | 8 | 5 | 1 | 5 | 2 | 9 | 2 | 6 |
| | 0.5 | 2 | 3 | 1 | 1 | 1 | 7 | 1 | 1 |
| 8 | 0.6 | 4 | 5 | 1 | 1 | 1 | 8 | 1 | 1 |
| | 2.5 | 8 | 7 | 4 | 8 | 8 | 9 | 3 | 4 |
| A | 0.6 | 9 | 8 | 8 | 9 | 9 | 9 | 6 | 7 |
| | 5.0 | 8 | — | 4 | 8 | 9 | 8 | 7 | 4 |
| B | 2.5 | 9 | — | 7 | 9 | 9 | 9 | 8 | 6 |

EXAMPLE III

Using a range of further compounds, the following results were obtained when employing the process according to Examples I and II in the pre-emergence and post-emergence methods:

| Example No. | kg of active substance/ha | Pre-emergence Matricaria | Pre-emergence Amaranthus | Post-emergence Matricaria | Post-emergence Amaranthus |
|---|---|---|---|---|---|
| 10 | 2.5 | — | 1 | — | 1 |
| | 0.6 | — | — | — | — |
| 12 | 2.5 | 1 | 1 | 1 | 1 |
| | 0.6 | 1 | 1 | 1 | 1 |
| 15 | 2.5 | 1 | 1 | 1 | 1 |
| | 0.6 | 1 | 1 | 3 | 1 |
| 16 | 2.5 | 4 | 1 | — | — |
| | 0.6 | — | 5 | — | — |
| 17 | 2.5 | 1 | 1 | — | — |
| | 0.6 | 1 | 1 | — | — |
| 18 | 2.5 | 1 | 1 | — | — |
| | 0.6 | 1 | 1 | — | — |
| 19 | 2.5 | 1 | 1 | — | — |
| | 0.6 | 2 | 1 | — | — |
| 21 | 2.5 | 3 | 1 | — | — |
| | 0.6 | 4 | 1 | — | — |
| 22 | 2.5 | 1 | 1 | — | — |
| | 0.6 | 1 | 1 | — | — |
| 24 | 2.5 | — | 1 | — | — |
| | 0.6 | — | 1 | — | — |
| 39 | 2.5 | 1 | 1 | 1 | 1 |
| | 0.6 | 1 | 1 | 1 | 1 |
| 50 | 2.5 | 1 | 1 | 1 | 1 |
| | 0.6 | 1 | 1 | 1 | 1 |
| 51 | 2.5 | 1 | 1 | 1 | 1 |
| | 0.6 | 1 | 2 | 2 | 1 |
| 52 | 2.5 | 1 | 1 | 1 | 1 |
| | 0.6 | 4 | 2 | 1 | 1 |
| 53 | 2.5 | 1 | 1 | 1 | 1 |
| | 0.6 | 1 | 1 | 1 | 1 |
| 54 | 2.5 | 1 | 1 | 3 | 1 |
| | 0.6 | 5 | 1 | 5 | 3 |
| 55 | 2.5 | 1 | 1 | 1 | 1 |
| | 0.6 | 1 | 1 | 2 | 1 |
| 64 | 2.5 | — | 1 | 1 | 1 |
| | 0.6 | — | 1 | 1 | 1 |
| 65 | 2.5 | — | 1 | — | — |
| | 0.6 | — | 2 | — | — |

We claim:

1. A compound of the general formula

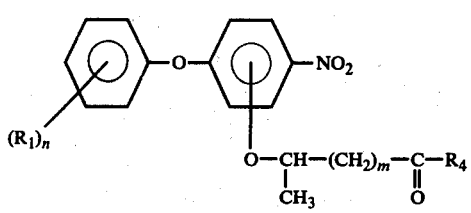

wherein
$R_1$ is Cl or Br;
$R_4$ is $(C_1-C_8)$ alkoxy which may be monosubstituted or disubstituted by halogen and/or $(C_1-C_2)$ OH; or OCat. with Cat. denoting a cation of Na, K or $NH_4$;
m is 0 or 1 and
n is 1 or 2.

2. A compound of the general formula

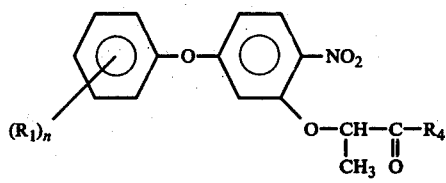

wherein $R_1$
is Cl or Br,
$R_4$ is $(C_1-C_8)$alkoxy and
n is 1 or 2.

3. The compound of the formula

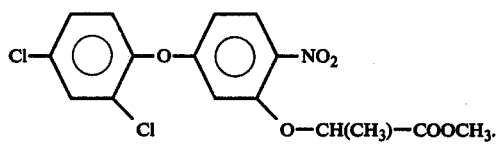

4. The compound of the formula

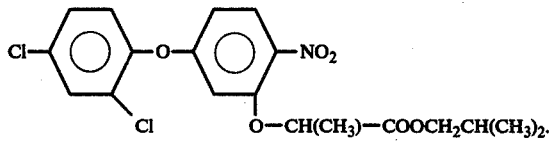

5. The compound of the formula

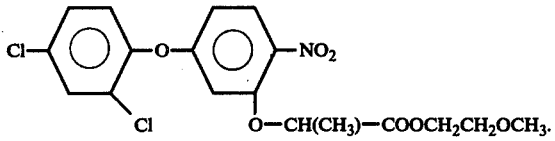

6. The compound of formula

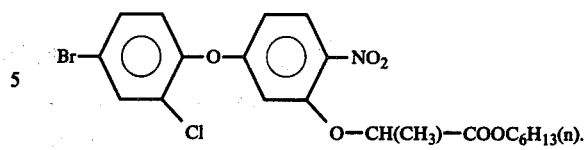

7. The compound of the formula

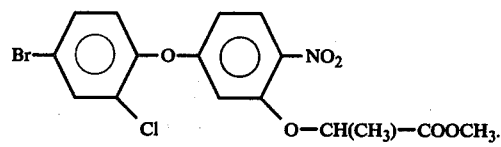

8. The compound of the formula

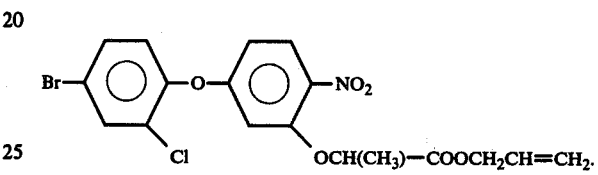

9. The compound of the formula

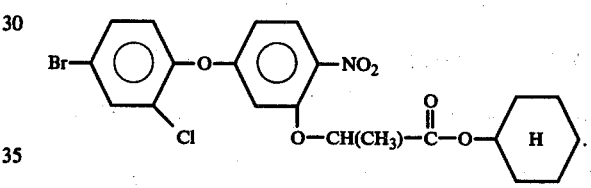

10. The compound of the formula

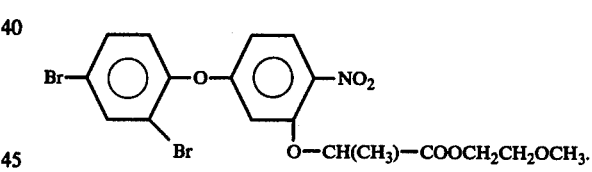

11. A herbicidal composition consisting essentially of an inert carrier and a herbicidally effective amount of a compound of the formula

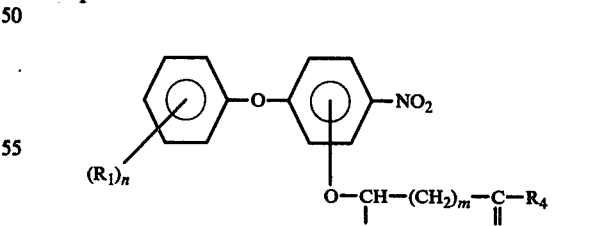

wherein
$R_1$ is Cl or Br;
$R_4$ is $(C_1-C_8)$ alkoxy which may be monosubstituted or disubstituted by halogen and/or $(C_1-C_2)$ alkoxy; OH; or OCat. with Cat. denoting a cation of Na, K or $NH_4$;
m is 0 or 1 and
n is 1 or 2.

12. An herbicidal composition consisting essentially of an inert carrier and an herbicidally effective amount of a compound of the formula:

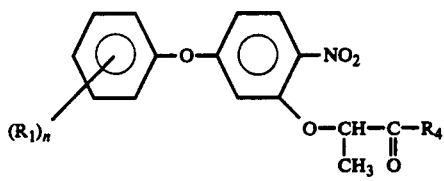

wherein $R_1$ is Cl and Br, $R_4$ is $(C_1-C_8)$alkoxy and n is 1 or 2.

13. The method of combating weed growth in a field planted with crops which comprises applying a herbicidally effective amount of a composition containing as its essential active ingredient a compound of the formula

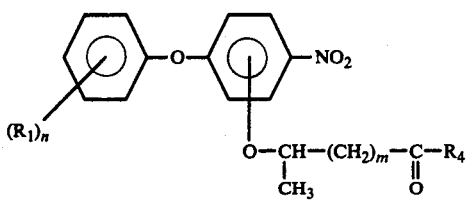

wherein
$R_1$ is Cl or Br;
$R_4$ is $(C_1-C_8)$ alkoxy which may be monosubstituted or disubstituted by halogen and/or $(C_1-C_2)$ alkoxy; OH, or OCat. with Cat. denoting a cation of Na, K or $NH_4$;
m is 0 or 1 and
n is 1 or 2.

14. The method of combating weed growth in a field planted with crops which comprises applying an herbicidally effective amount of a composition containing as its essential active ingredient a compound of the formula:

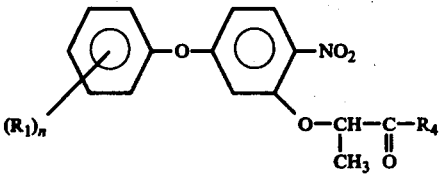

wherein
$R_1$ is Cl or Br,
$R_4$ is $(C_1-C_8)$alkoxy and
n is 1 or 2.

* * * * *

UNITED STATES PATENT AND TRADEMARK OFFICE
CERTIFICATE OF CORRECTION

PATENT NO. : 4,134,753
DATED : January 16, 1979
INVENTOR(S) : Horlein et al.

It is certified that error appears in the above-identified patent and that said Letters Patent are hereby corrected as shown below:

Column 13, line 16 (Claim 1, fourth line after the structural formula), "$(C_1-C_2)OH$" should be --$(C_1-C_2)$ alkoxy; OH--.

Signed and Sealed this

Thirtieth Day of December 1980

[SEAL]

Attest:

SIDNEY A. DIAMOND

Attesting Officer

Commissioner of Patents and Trademarks